United States Patent [19]

Yamanaka et al.

[11] Patent Number: 4,709,095

[45] Date of Patent: Nov. 24, 1987

[54] ORTHO-AMINOMETHYLPHENOL COMPOUNDS

[75] Inventors: Tsutomu Yamanaka, Nakatsu; Osamu Yaoka, Chikujo, both of Japan

[73] Assignee: Yoshitomi Pharmaceutical Industries, Ltd., Osaka, Japan

[21] Appl. No.: 853,809

[22] PCT Filed: Aug. 2, 1985

[86] PCT No.: PCT/JP85/00440

§ 371 Date: Mar. 25, 1986

§ 102(e) Date: Mar. 25, 1986

[87] PCT Pub. No.: WO86/01201

PCT Pub. Date: Feb. 27, 1986

[30] Foreign Application Priority Data

Aug. 6, 1984 [JP] Japan .................................. 59-164460

[51] Int. Cl.$^4$ ...................... A61K 31/15; C07C 131/00
[52] U.S. Cl. ...................................... 564/253; 564/256; 564/257; 564/265; 514/456; 514/640
[58] Field of Search ............... 564/253, 256, 257, 265; 549/397; 514/640, 456

[56] References Cited

U.S. PATENT DOCUMENTS 3,692,835  9/1972  Van Dijk et al. .................... 564/256
3,864,401  2/1975  Schultz et al. ...................... 564/390
4,071,686  1/1978  Van Dijk et al. ..................... 560/35

FOREIGN PATENT DOCUMENTS 0001428  4/1979  European Pat. Off. ............ 514/456

OTHER PUBLICATIONS

Conant, James Bryant et al., *The Chemistry of Organic Compounds*, 4th Ed., (1954), The MacMillan Company, Publ. at p. 113.

*Primary Examiner*—James H. Reamer
*Attorney, Agent, or Firm*—Wenderoth, Lind & Ponack

[57] ABSTRACT

Ortho-aminomethylphenol compounds of the formula:

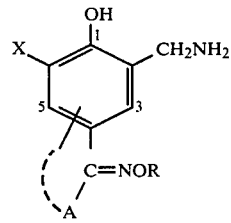

wherein X is hydrogen or halogen, R is hydrogen or alkyl having 1 to 4 carbon atoms and A is alkyl having 1 to 4 carbon atoms, phenyl, benzyl or a bivalent radical selected from —$(CH_2)_3$— and —$O(CH_2)_2$— and joined together with the 3 or 5 position of the benzene nucleus to form a bicycle, or pharmaceutically acceptable salts thereof, a method of preparing said compounds and a pharmaceutical composition containing said compounds, are disclosed.

Such compounds exhibit antiinflammatory, analgesic, diuretic and antihypertensive activities, so they are useful in the treatment for diseases caused by inflammation, edema or hypertension.

9 Claims, No Drawings

ORTHO-AMINOMETHYLPHENOL COMPOUNDS

FIELD OF THE INVENTION

The present invention relates to novel and pharmaceutically useful ortho-aminomethylphenol compounds or pharmaceutically acceptable salts thereof, a method of preparing said compounds and a pharmaceutical composition containing said compounds.

BACKGROUND OF THE INVENTION

2-Aminomethyl-4-tertiary-butyl-6-iodophenol hydrochloride (MK-447) possessing saluretic, diuretic, hypotensive and antiinflammatory activities is disclosed in Journal of Medicinal Chemistry, vol. 23, p. 1414 (1980), and 2-aminomethyl-4-tertiary-butyl-6-methylsulfonylphenol (Hoe-365) possessing diuretic, saluretic and antihypertensive activities is disclosed in European Patent Application No. 88346.

DISCLOSURE OF THE INVENTION

The present inventors paid attention to the above prior arts and intensively investigated to prepare pharmaceutical compounds with more preferable properties such as higher safety and more potent activities.

As a result of such investigations, the present inventors have found that ortho-aminomethylphenol compounds having an oxime group in the 4 position to the hydroxyl group exhibit significantly pharmacological activities, and have completed the present invention.

The present invention relates to ortho-aminomethylphenol compounds of the formula:

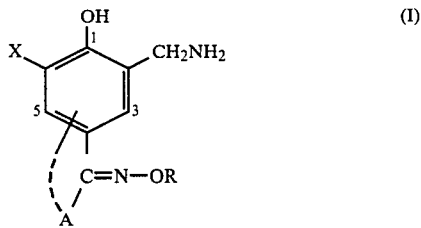

wherein X is hydrogen or halogen (chlorine, bromine, iodine or fluorine), R is hydrogen or alkyl having 1 to 4 carbon atoms (e.g. methyl, ethyl, propyl, isopropyl, butyl, isobutyl or tertiary-butyl), A is alkyl having 1 to 4 carbon atoms (e.g. methyl, ethyl, propyl, isopropyl, butyl, isobutyl or tertiary-butyl), phenyl, benzyl or a bivalent radical selected from —(CH$_2$)$_3$— and —O(CH$_2$)$_2$— and joined together with the 3 or 5 position of the benzene nucleus to form a bicycle, or pharmaceutically acceptable salts thereof, a method of preparing said compounds and a pharmaceutical composition containing said compounds.

Preferable compounds of the present invention are the compounds of formula (I) wherein X is chlorine, bromine or iodine, R is hydrogen or alkyl having 1 to 4 carbon atoms and A is alkyl having 1 to 4 carbon atoms.

The compounds of formula (I) can be, for example, prepared by reacting a compound of the formula:

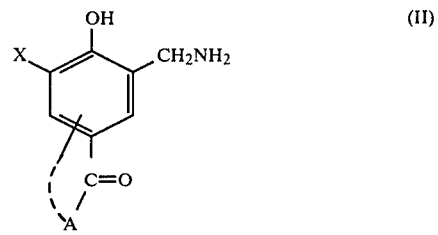

with a compound of the formula:

$$H_2N-OR \qquad (III)$$

The reaction is usually carried out by using an acid addition salt (e.g. hydrochloride) of the compound of formula (III) in an inert solvent in the presence of an alkali hydroxide or an organic base. The obtained compounds can be, if necessary, purified by a conventional manner such as reprecipitation, recrystallization or a column chromatography.

While the compounds of formula (I) may occur geometrical isomers of syn and anti isomers (E and Z isomers) with respect to the oxime group (—C=N—OR), whichever of these isomers and the mixtures thereof can be included in the present invention.

The compounds of formula (I) can be, if desired, converted into salts with sodium, potassium, magnesium, calcium, aluminum or an amine with respect to phenol or oxime, or salts with an inorganic acid (e.g. hydrochloric acid, hydrobromic acid or sulfuric acid) or an organic acid (e.g. oxalic acid, maleic acid, succinic acid, fumaric acid or tartaric acid) with respect to the amino group.

The starting compounds of formula (II) wherein X is hydrogen can be, for example, prepared by subjected a compound of the formula:

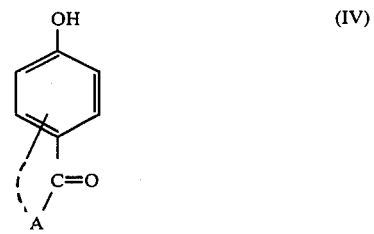

to an amidomethylation reaction and then hydrolysis. The compounds of formula (II) wherein X is halogen can be prepared by reacting the obtained compound with halogen or a halogenating agent to introduce halogen atom into the 6 position of the benzene nucleus.

The starting compounds can also be prepared by halogenating the compound of formula (IV) and then aminomethylating the obtained compound. The product is identical with the compound prepared by the above method or position isomer with respect to the substituent of X and the aminomethyl group. These compounds can be distinguished one from the other based on their properties on spectrum.

The compounds of the present invention and salts thereof have antiinflammatory activity, analgesic activity, diuretic activity and antihypertensive activity, so they are useful in the treatment for various diseases caused by inflammation, edema or hypertension.

The following pharmacological experiments and toxicological experiments illustrate the activities or effects of the compounds of the present invention. The test compounds employed are as follows:

Test compound A: 3'-aminomethyl-5'-bromo-4'-hydroxypropiophenone oxime

Test compound B: 3'-aminomethyl-5'-bromo-4'-hydroxypropiophenone O-methyloxime

Test compound C: 3'-aminomethyl-4'-hydroxy-5'-iodopropiophenone O-methyloxime

Test compound D: 3'-aminomethyl-4'-hydroxy-5'-iodopropiophenone oxime

Test compound E: 3'-aminomethyl-5'-chloro-4'-hydroxypropiophenone O-methyloxime

Test compound F: 3'-aminomethyl-5'-chloro-4'-hydroxypropiophenone oxime monohydrate Pharmacological experiment 1: Diuretic activity Groups of 6 male Wistar rats, weighing 180–220 g were not fed with any food for 18 hours, and further with any food and water for 3 hours.

After 25 ml/kg of a suspension of a test compound in a 0.9% aqueous sodium chloride solution were orally administered, the rats were placed in a cage for collecting urine. The urine excreted was collected for 6 hours after the administration of test compound. The urine volume, and concentration of sodium, potassium and chlorine ions in urine were measured. The concentrations of urinary sodium and potassium ions were determined with a flame photometer and concentration of chlorine ion was determined with a chloride counter.

The results are summarized in Table 1. The values in Table are represented as mean value ±standard error, and the values with * (asterisk) mean that they are statistically significant as compared to the control group at $p<0.01$.

TABLE 1

|  | Dose mg/kg p.o. | Urine volume (ml/100 g/6 hr) | Excretion of electrolytes (μeq/100 g/6 hr) | | | Na/K |
|---|---|---|---|---|---|---|
|  |  |  | Na | K | Cl |  |
| Test Compound A | 0 | 0.6 ± 0.1 | 135 ± 23 | 54 ± 9 | 150 ± 21 | 2.6 ± 0.4 |
|  | 1.0 | 3.3 ± 0.1* | 474 ± 14* | 115 ± 6* | 540 ± 11* | 4.2 ± 0.3* |
| Test Compound B | 0 | 0.8 ± 0.1 | 152 ± 27 | 75 ± 6 | 176 ± 28 | 2.0 ± 0.3 |
|  | 1.0 | 2.3 ± 0.3* | 356 ± 41* | 102 ± 11* | 401 ± 47* | 3.7 ± 0.5* |
| Test Compound C | 0 | 1.1 ± 0.1 | 195 ± 26 | 72 ± 8 | 198 ± 28 | 2.7 ± 0.2 |
|  | 1.0 | 2.9 ± 0.2* | 443 ± 34* | 132 ± 13* | 475 ± 37* | 3.5 ± 0.3* |
| Test Compound D | 0 | 0.9 ± 0.2 | 142 ± 19 | 44 ± 7 | 173 ± 18 | 3.6 ± 0.7 |
|  | 1.0 | 5.0 ± 0.5* | 455 ± 37* | 80 ± 6* | 518 ± 30* | 5.9 ± 0.6* |
| Test Compound E | 0 | 0.7 ± 0.1 | 126 ± 14 | 63 ± 5 | 138 ± 18 | 2.0 ± 0.2 |
|  | 1.0 | 3.0 ± 0.3* | 384 ± 30* | 111 ± 8* | 447 ± 36* | 3.5 ± 0.3* |
| Test Compound F | 0 | 1.5 ± 0.2 | 260 ± 34 | 93 ± 8 | 256 ± 29 | 2.9 ± 0.4 |
|  | 1.0 | 3.3 ± 0.2* | 509 ± 26* | 123 ± 8* | 547 ± 32* | 4.2 ± 0.3* |

Pharmacological experiment 2: Antihypertensive activity

Groups of male and 20–25 week-old spontaneously hypertensive rats (SHR), weighing 380–400 g were used.

Blood pressure and heart rate were measured according to a tail cuff method with an indirect blood pressure measuring apparatus before and after 5 hours after the oral administration of 30 mg/kg of a test compound.

The results are summarized in Table 2. The values in Table are represented as mean value ± standard error.

TABLE 2

|  | Blood pressure (mmHg) | | Heart rate (beats/min) | |
|---|---|---|---|---|
|  | Before administration | Change of blood pressure after 5 hour | Before administration | After 5 hour |
| Test Compound A | 227 ± 7 | −20 ± 8 | 375 ± 20 | 369 ± 19 |
| Test Compound B | 217 ± 5 | −37 ± 8 | 313 ± 11 | 332 ± 5 |
| Test Compound C | 226 ± 5 | −22 ± 6 | 355 ± 13 | 360 ± 10 |
| Test Compound D | 234 ± 5 | −44 ± 9 | 369 ± 9 | 365 ± 9 |
| Test Compound E | 234 ± 3 | −49 ± 2 | 336 ± 11 | 346 ± 8 |
| Test Compound F | 218 ± 8 | −26 ± 10 | 364 ± 7 | 350 ± 8 |

Toxicological experiment

To a group of five male ddY mice weighing 20–28 g were intraperitoneally administered each of 300 mg/kg of test compounds A, B and E. All of mice survived for 5 days.

Since the compounds of the present invention, when used as diuretics or antiedematic agents, exhibit low toxicity compared to MK-447 and less nervous effects or other undesirable effects, they have more preferable properties such as higher safety for long administration and show less potassium excretion in urine. Therefore, the compounds of the present invention are more potent as diuretics.

The compounds of the present invention used as drugs can be safely administered to the patients in the form of tablets, capsules, granules, powder or injectable solutions by admixing with excipient, diluent or carrier. The daily doses for human adults range 0.1–500 mg, but may vary depending on the severity of diseases, or age or body weight of patients.

Pharmaceutical preparation: film-coated tablets containing 10 mg of active ingredient

| (a) composition of tablets | |
|---|---|
| Compound of Example 1 | 10.0 mg |
| Lactose | 70.0 mg |
| Starch | 20.5 mg |
| Microcrystalline cellulose | 15.0 mg |
| Talc | 4.0 mg |
| Magnesium stearate | 0.5 mg |
| (b) composition of film coating agent | |
| Hydroxypropylmethycellulose | 2.7 mg |
| Polyethylene glycol 6000 | 0.3 mg |

The compound of Example 1 as an active ingredient, lactose, starch and microcrystalline cellulose are kneaded with a binder prepared by starch, granulated and dried at 50° C. The dry granules are forced through a 24 mesh sieve and mixed with talc and magnesium stearate. The mixture is compressed with a punch with a diameter of 6 mm into tablets weighing 120 mg each. The tablets are film-coated by using hydroxypropylmethylcellulose and polyethylene glycol 6000 to obtain film-coated tablets weighing 123 mg each.

The following examples explain the present invention in more detail, but they are not to be construed as limiting the present invention.

REFERENCE EXAMPLE 1

To 40 ml of concentrated sulfuric acid with stirring under ice-cooling is added a mixture of 10 g of 4'-hydroxypropiophenone and 10 g of N-hydroxymethylchloroacetic amide in a small portion. After addition, the reaction mixture is further stirred under ice-cooling for 130 minutes. The resulting mixture is poured into ice-cold water containing sodium chloride and the solution is extracted with ethyl acetate. The ethyl acetate layer is washed with water and dried over sodium sulfate and then filtered. The filtrate is concentrated under reduced pressure and obtained white crystals are recrystallized from a mixture of hexane and ethanol to give 9.6 g of 3'-chloroacetamidomethyl-4'-hydroxypropiophenone as white crystals, melting at 143°–145° C.

The crystals (32 g) are suspended in 50 ml of concentrated hydrochloric acid and 70 ml of water, and refluxed with heating for about 25 minutes. The hot solution is filtered and the filtrate is allowed to stand by ice-cooling to obtain 22 g of 3'-aminomethyl-4'-hydroxypropiophenone hydrochloride as white crystals, melting at 237°–238° C. with decomposition.

3'-Aminomethyl-4'-hydroxyacetophenone hydrochloride, melting at 243°–244° C. with decomposition (recrystallized from water) can be obtained from 4'-hydroxyacetophenone in a similar manner.

REFERENCE EXAMPLE 2

To a solution of 22 g of 3'-aminomethyl-4'-hydroxypropiophenone hydrochloride in 300 ml of ice-cold water is added dropwise 17 g of bromine with stirring under ice cooling for about 10 minutes. After addition, the reaction mixture is stirred under ice cooling for 3 minutes and then at room temperature for 5 minutes. To the resulting mixture is added 200 ml of water and insoluble substances are filtered off. The filtrate is neutralized with powdery sodium hydrogencarbonate and the liquid layer is adjusted pH to about 7 to precipitate fine powder. The powder is collected by filtration and dried to give 25 g of 3'-aminomethyl-5'-bromo -4'-hydroxypropiophenone, melting at 186°–187° C. with decomposition.

3'-Aminomethyl-5'-bromo-4'-hydroxy-acetophenone, melting above 300° C. can be obtained from 3'-aminomethyl-4'-hydroxyacetophenone in a similar manner.

REFERENCE EXAMPLE 3

To a suspension of 35 g of 6-hydroxy-1-tetralone and 34 g of N-hydroxymethylchloroacetic amide in 140 ml of acetic acid with stirring under ice cooling is added portionwise 40 ml of concentrate sulfuric acid.

The mixture is stirred under ice cooling for 30 minutes and at room temperature for 3 hours and then allowed to stand overnight. The resulting mixture is poured into ice-cold water and stirred to solidify. The solid is collected by filtration and dried and then extracted with boiling ethanol. Insoluble substances are filtered off and the filtrate is concentrated under reduced pressure. The residue is recrystallized from a mixture of ethanol and ethyl acetate to give 25.4 g of 5-chloroacetamidomethyl-6-hydroxy -3,4-dihydro-1(2H)-naphthalenone, melting at 196°–199° C.

A suspension of 22.4 g of this compound in 35 ml of concentrated hydrochloric acid and 50 ml of water is refluxed with heating for 35 minutes. The reaction mixture is completely dried under reduced pressure. The residue is washed with ethanol and collected by filtration to give 17.3 g of 5-aminomethyl-6-hydroxy-3,4-dihydro-1(2H)-naphthalenone hydrochloride, melting above 300° C.

To a solution of 12.0 g of the hydrochloride in 20 ml of acetic acid and 15 ml of water with stirring under ice cooling is added dropwise 9.3 g of bromine for 15 minutes. After addition, the mixture is stirred under ice cooling for 5 minutes and ice-cold water is added. The mixture is extracted with ethyl acetate and the aqueous layer is neutralized with powdery sodium hydrogencarbonate. The separated insoluble substance is collected by filtration and dried to give 10.5 g of 5-aminomethyl-7-bromo-6hydroxy-3,4-dihydro-1(2H)-naphthalenone, melting above 00° C.

REFERENCE EXAMPLE 4

To a solution of 4.3 g of 6-hydroxy-1-teralone in 0 ml of acetic acid and 6 ml of water with stirring under ice cooling is added dropwise a solution of 5.1 g of bromine in acetic acid for 8 minutes. After addition, the mixture is stirred unde ice cooling for 5 minutes and at room temperature for 30 minutes. To the reaction mixture is added 170 ml of ice-cold water. The insoluble substance is collected by filtration, dried and recrystallized from a mixture of hexane, ethyl acetate and ethanol to give 4.8 g of 5-bromo-6-hydroxy-3,4-dihydro-1(2H)-naphthalenone, melting at 183°–186° C.

To a solution of 2.0 g of this compound and 2.6 g of N-hydroxymethylchloroacetic amide in 8.0 ml of acetic acid is added 20 ml of concentrated sulfuric acid at room temperature, and then stirred at 40° C. for 3 hours. The reaction mixture is poured into ice-cold water and stirred. The insoluble substance is collected by filtration and dried and then dissolved in 7 ml of dimethylformamide. To the solution is added 21 ml of water and separated insoluble substance is collected by filtration to give 1.5 g of 5-bromo-7-chloroacetoamidomethyl -6-hydroxy-3,4-dihydro-1(2H)-naphthalenone, melting at 201°–203° C.

A suspension of 2.1 g of this compound in 20 ml of acetic acid, 10 ml of concentrated hydrochloric acid and 5 ml of water is refluxed with heating for about 65 minutes and concentrated under reduced pressure. To the residue are added 30 ml of water and activated charcoal, and the mixture is filtered. The filtrate is adjusted to pH about 7 with sodium hydrogencarbonate. The precipitated substance is collected by filtration and dried to give 1.4 g of 7-aminomethyl-5-bromo-6-hydroxy-3,4-dihydro-1(2H)-naphthalenone, melting above 300° C.

REFERENCE EXAMPLE 5

3-Aminomethyl-4-hydroxybenzophenone hydrochloride, melting at 217°–218° C. with decomposition can be obtained from 4-hydroxybenzophenone in a similar manner described in Reference example 3, and 3-aminomethyl-5-bromo-4-hydroxybenzophenone, melting at 187°–189.5° C. with decomposition can be obtained by bromination the above compound.

REFERENCE EXAMPLE 6

To a solution of 5.0 g of 3'-aminomethyl-4'-hydroxypropiophenone hydrochloride in 225 ml of water are added 7.0 g of potassium carbonate and 7.0 g of potassium iodide, and then is added 6.4 g of iodine at room temperature. The mixture is stirred further at room temperature for about 2 hours and adjusted to pH 8 with hydrochloric acid. The insoluble solid is collected by filtration and dried and then recrystallized from ethanol to give 5.8 g of 3'-amino-methyl-4'-hydroxy-5'-iodopropiophenone, melting at 191°–192.5° C. with decomposition.

REFERENCE EXAMPLE 7

A mixture of 12.0 g of 3'-chloro-4'-hydroxypropiophenone and 14.0 g of N-hydroxymethylchloroacetic amide is added portionwise to 60 ml of concentrated sulfuric acid with stirring under ice cooling for 15 minutes. After addition, the mixture is stirred at 30°–35° C. for 3 hours and the resulting mixture is poured into ice-cold water. The viscous semi-solid formed is washed with ice-cold water, and to the mixture are added 20 ml of ethanol, 10 ml of water and 30 ml of concentrated hydrochloric acid and then refluxed with heating for 3 hours. The resulting mixture is cooled to room temperature and 200 ml of water is added. After the small amount of insoluble substance is filtered off and the filtrate is adjusted to pH 7–8 with sodium hydrogencarbonate and amorphous precipitate is collected by filtration. The precipitate is reprecipitated with a large amount of water and collected by filtration and then dried to give 5.6 g of 3'-aminomethyl-5'-chloro-4'-hydroxypropio-hydroxypropiophenone phenone, melting at 186°–188° C. with decomposition.

EXAMPLE 1

A solution of 9.0 g of 3'-aminomethyl-5'-bromo-4'-hydroxypropiophenone and 7.0 g of hydroxylamine hydrochloride in 50 ml of 4N sodium hydroxide solution and 15 ml of ethanol is refluxed with heating for 40 minutes. To the reaction mixture is added activated charcoal and the charcoal is filtered off and then the mixture is adjusted to pH 6–7 with concentrated hydrochloric acid. After allowing to stand at room temperature, the precipitate is collected by filtration, washed with water and dried to give 8.1 g of 3'-aminomethyl-5'-bromo-4'-hydroxypropiophenone oxime, melting at 174°–175° C. with decomposition.

EXAMPLE 2

A solution of 9.0 g of 3'-aminomethyl-5'-bromo-4'-hydroxypropiophenone and 9.0 g of O-methylhydroxylamine hydrochloride in 80 ml of pyridine and 40 m of ethanol is refluxed with heating for 25 minutes. Activated charcoal is added to the reaction mixture and then filtered off. The filtrate is concentrated under reduced pressure and to the residue are added 200 ml of ice-cold water and 6.0 g of sodium hydrogencarbonate and stirred. The insoluble substance is collected by filtration and washed with water and then dried to give 7.9 g of 3'-aminomethyl-5'-bromo-4'-hydroxypropiophenone O-methyloxime as fine powdery solid, melting at 178°–178.5° C. with decomposition.

EXAMPLE 3

A mixture of 2.0 g of 3'-aminomethyl-4'-hydroxy-5'-iodopropiophenone and 1.2 g of hydroxylamine hydrochloride is added to 10 ml of 4N sodium hydroxide solution and 3.5 ml of ethanol, and then the mixture is refluxed with heating for 45 minutes. After cooling to room temperature, 15 ml of water is added to the reaction mixture. After filtration of the mixture, the filtrate is stirred under ice cooling and adjusted to pH 7.5 with concentrated hydrochloric acid. The white fine powder precipitated is collected by filtration, washed with cold water and dried to give 2.0 g of 3'-aminomethyl -4'-hydroxy-5'-iodopropiophenone oxime monohydrate, melting at 167°–168° C. with decomposition.

3'-Aminomethyl-5'-chloro-4'-hydroxypropiophenone oxime, melting at 174°–175° C. with decomposition (recrystallized from ethanol) can be prepared from 3'-aminomethyl-5'-chloro -4'-hydroxypropiophenone in a similar manner.

EXAMPLE 4

To a solution of 2.0 g of 3'-aminomethyl-4'-hydroxy5'-iodopropiophenone in 15 ml of pyridine and 7 ml of ethanol is added 1.4 g of O-methylhydroxylamine hydrochloride, and the mixture is refluxed with heating for 45 minutes. The reaction mixture is treated with activated charcoal and filtered. The filtrate is concentrated under reduced pressure and to the residue is added ice-cold water. To the mixture is added 1.4 g of sodium hydrogencarbonate and stirred. The precipitated crystals are collected by filtration, washed with water and then recrystallized from methanol to give 1.2 g of 3'-aminomethyl-4'-hydroxy-5'-iodopropiophenone O-methyloxime, melting at 156°–157° C. with decomposition.

3'-Aminomethyl-5'-chloro-4'-hydropropiophenone O-methyloxime, melting at 178.5°–179° C. (recrystalized from ethanol) can be prepared from the corresponding propiophenone compound in a similar manner.

The following compounds can be prepared in a similar manner described in the above examples:

3'-Aminomethyl-4'-hydroxyacetophenone oxime, melting at 175.5°–176.0° C. with decomposition 3'-Aminomethyl-5'-bromo-4'-hydroxyacetophenone oxime ethanolate, melting at 186°–187° C. with decomposition 3'-Aminomethyl-5'-bromo-4'-hydroxyacetophenone O-methyloxime -monohydrate, melting at 209°–212° C. with decomposition 3'-Aminomethyl-5'-bromo-4'-hydroxy-2methylpropiophenone oxime hemihydrate, melting at 179°–180° C. with decomposition 3'-Aminomethyl-5'-bromo-4'-hydroxy-2-methylpropiophenone O-methyloxime hemihydrate, melting at 163.5°–165° C. with decomposition 3'-Aminomethyl-5'-bromo-4'-hydroxypentanophenone oxime, melting at 139-141° C. with decomposition 3'-Aminomethyl-5'-bromo-4'-hydroxypentanophenone O-methyloxime -dihydrate, melting at 221–222° C. with decomposition 3-Aminomethyl-5-bromo4-hydroxybenzophenone oxime, melting at 175°–176° C. with decomposition 3-Aminomethyl-5-bromo-4-hydroxybenzophenone O-methyloxime, melting at 152–153° C. with decomposition 3-Aminomethyl-5-bromo-4-hydroxydeoxybenzoin oxime sesquihydrate, melting at 212°–215° C. with decomposition 3-Aminomethyl-5-bromo-4-hydroxydeoxybenzoin O-methyloxime 5-Aminomethyl-7-bromo-6-hydroxy-3,4-dihydro-1(2H)-naphthalenone oxime, decomposing gradually from about 210° C. and not showing clear melting point nor decomposing point 5-Aminomethyl-7-bromo-6-hydroxy-3,4-dihydro-1(2H)-naphthalenone O-methyloxime, melting at 177–178° C. with decomposition 7-Aminomethyl-5-bromo-6-hydroxy-3,4-dihydro-1(2H)-naphthalenone oxime, melting above 300° C.

6-Aminomethyl-8-bromo-7-hydroxy-4-chromanone oxime, melting above 300° C.

6-Aminomethyl-8-bromo-7-hydroxy-4-chromanone O-methyloxime hemihydrate, melting at 187°–189° C. with decomposition 8-Aminomethyl-6-bromo-7-hydroxy-4-chromanone oxime, melting above 300° C.

8-Aminomethyl-6-bromo-7-hydroxy-4-chromanone O-methyloxime, melting at 194–196° C. with decomposition Although the present invention has been adequately discussed in the foregoing specification and examples included therein, one readily recognizes that various changes and modifications ma be made without departing from the spirit and scope thereof.

What is claimed is:

1. An ortho-aminomethylphenol compound of the formula:

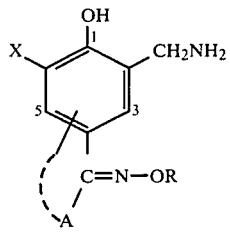

or a pharmaceutically acceptable salt thereof, wherein X is hydrogen or halogen, R is hydrogen or alkyl having 1 to 4 carbon atoms and A is alkyl having 1 to 4 carbon atoms, phenyl, benzyl or a bivalent radical selected from —(CH$_2$)$_3$— and —O(CH$_2$)$_2$—and joined together with the 3 or 5 position of the benzene nucleus to form a bicycle.

2. The compound of claim 1 wherein X is chlorine, bromine or iodine, R is hydrogen or alkyl having 1 to 4 carbon atoms and A is alkyl having 1 to 4 carbon atoms.

3. The compound of claim 1:
3'-Aminomethyl-5'-bromo-4'-hydroxypropiophenone oxime.

4. The compound of claim 1:
3'-Aminomethyl-5'-bromo-4'-hydroxypropiophenone O-methyloxime.

5. The compound of claim 1:
3'-Aminomethyl-4'-hydroxy-5'-iodopropiophenone oxime, 6. The compound of claim 1:
3'-Aminomethyl-4'-hydroxy-5'-iodopropiopheenone O-methyloxime.

7. The compound of claim 1:
3'-Aminomethyl-5'-chloro-4'-hydroxypropiophenone oxime.

8. The compound of claim 1:
3'-Aminomethyl-5'-chloro-4'-hydroxypropiophenone O-methyloxime.

9. A pharmaceutical composition for the treatment of a disease caused by inflammation, edema or hypertension comprising a therapeutically effective amount of a compound of claim 1 or a pharmaceutically acceptable salt thereof and a pharmaceutically acceptable salt.

* * * * *